(12) United States Patent
Kang et al.

(10) Patent No.: US 9,907,696 B2
(45) Date of Patent: Mar. 6, 2018

(54) FIBER OPTIC DISTAL SENSOR CONTROLLED MICRO-MANIPULATION SYSTEMS AND METHODS

(71) Applicant: The Johns Hopkins University, Baltimore, MD (US)

(72) Inventors: Jin U. Kang, Ellicott City, MD (US); Peter L. Gehlbach, Monkton, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 229 days.

(21) Appl. No.: 14/256,695

(22) Filed: Apr. 18, 2014

(65) Prior Publication Data

US 2015/0297404 A1    Oct. 22, 2015

(51) Int. Cl.
*A61F 9/00* (2006.01)
*A61F 9/007* (2006.01)
(Continued)

(52) U.S. Cl.
CPC ........ *A61F 9/00736* (2013.01); *A61B 5/0073* (2013.01); *A61B 5/0066* (2013.01); *A61B 5/7207* (2013.01); *A61F 9/0133* (2013.01)

(58) Field of Classification Search
CPC .. A61F 9/00736; A61F 9/0133; A61B 5/0066; A61B 5/0073; A61B 5/7207
(Continued)

(56) References Cited

U.S. PATENT DOCUMENTS 6,468,265 B1    10/2002    Evans et al.
6,858,003 B2    2/2005    Evans et al.
(Continued)

FOREIGN PATENT DOCUMENTS

JP          4354601 B2    10/2009
WO    WO-2006014392 A1    2/2006
(Continued)

OTHER PUBLICATIONS

Ahmad et al., "Cross-correlation-based image acquisition technique for manually-scanned optical coherence tomography," Opt. Express 17(10), 8125-8136 (2009).
(Continued)

*Primary Examiner* — Diane Yabut
*Assistant Examiner* — Martin T Ton
(74) *Attorney, Agent, or Firm* — Venable LLP; Henry J. Daley (57) ABSTRACT

A motion-compensated cutting system includes a hand-held tool body, and an actuator connected to the tool body. A shaft of the actuator is movable relative to the tool body so that a distal end of a cutting implement attached to the shaft is axially movable relative to the tool body. An optical coherence tomography system includes an optical fiber with a distal end fixed relative to the distal end of the cutting implement. The system includes a control unit that can determine a position of the distal end of the cutting implement relative to a reference surface based on input from the optical coherence tomography system. The control unit can control the cutting implement to compensate for relative motion between the tool body and the reference surface, and can maintain a predetermined depth of the distal end of the cutting implement with respect to the reference surface.

22 Claims, 6 Drawing Sheets

(51) Int. Cl.
*A61B 5/00* (2006.01)
*A61F 9/013* (2006.01)

(58) Field of Classification Search
USPC .................................................. 606/130, 166
See application file for complete search history.

(56) References Cited

U.S. PATENT DOCUMENTS

| | | | |
|---|---|---|---|
| 7,933,024 | B2 | 4/2011 | Hirose |
| 8,375,808 | B2 | 2/2013 | Blumenkranz et al. |
| 2001/0024320 | A1 | 9/2001 | Okada |
| 2002/0163715 | A1 | 11/2002 | Engelhardt et al. |
| 2004/0111183 | A1 | 6/2004 | Sutherland et al. |
| 2004/0171334 | A1 | 9/2004 | Turnac et al. |
| 2005/0027199 | A1* | 2/2005 | Clarke ................. A61B 5/0066 600/473 |
| 2005/0029978 | A1 | 2/2005 | Oleynikov et al. |
| 2007/0076217 | A1 | 4/2007 | Baker et al. |
| 2007/0081732 | A1 | 4/2007 | Makiyama et al. |
| 2008/0218770 | A1* | 9/2008 | Moll ................... A61B 19/2203 356/614 |
| 2008/0278781 | A1 | 11/2008 | Sander |
| 2009/0196477 | A1 | 8/2009 | Cense et al. |
| 2009/0253985 | A1 | 10/2009 | Shachar et al. |
| 2009/0326556 | A1* | 12/2009 | Diolaiti .............. A61B 1/00009 606/130 |
| 2010/0036393 | A1* | 2/2010 | Unsworth .............. A61B 19/22 606/130 |
| 2010/0228123 | A1* | 9/2010 | Brennan .............. A61B 5/0066 600/437 |
| 2011/0295267 | A1* | 12/2011 | Tanner ................... B25J 9/1689 606/130 |
| 2012/0172893 | A1* | 7/2012 | Taylor ................ A61B 1/00172 606/130 |
| 2012/0182392 | A1* | 7/2012 | Kearns ................... B25J 11/009 348/46 |
| 2014/0078512 | A1 | 3/2014 | Kang et al. |
| 2014/0094968 | A1 | 4/2014 | Taylor et al. |

FOREIGN PATENT DOCUMENTS

| | | | |
|---|---|---|---|
| WO | WO-2006077107 | A1 | 7/2006 |
| WO | WO-2008091755 | A1 | 7/2008 |
| WO | WO-2008137710 | A1 | 11/2008 |
| WO | WO-2011091369 | A1 | 7/2011 |
| WO | WO-2011115627 | A1 | 9/2011 |
| WO | WO-2011139895 | A1 | 11/2011 |
| WO | WO-2012/012540 | A2 | 1/2012 |
| WO | WO 2012012540 | A3 * | 5/2012 ............. A61B 19/22 |
| WO | WO-2012/088320 | A2 | 6/2012 |

OTHER PUBLICATIONS

An and R. K. Wang, "In vivo volumetric imaging of vascular perfusion within human retina and choroids with optical micro-angiography," Opt. Express 16, 15 (2008).

Becker et al., "State estimation and feedforward tremor suppression for a handheld micromanipulator with a Kalman filter," IEEE/RSJ, International Conference on Intelligent Robots and Systems, 5160-6165(2011).

Benalcazar, W. Jung, and S. A. Boppart, "Aberration characterization for the optimal design of high-resolution endoscopic optical coherence tomography catheters," Opt.Lett. 37, 3 (2012).

Boppart et al., "Forward-imaging instruments for optical coherence tomography," Opt. Lett. 22 (21), 1618-1620 (1997).

Boppart et al., "Intraoperative assessment of microsurgery with three-dimensional optical coherence tomography," Radiology, vol. 208, pp. 81-86, 1998.

Boppart et al., "Optical coherence tomography: feasibility for basic research and image-guided surgery of breast cancer," Breast Cancer Res. Treatment 84(2), 85-97(2004).

Chen et al., "Noninvasive imaging of in vivo blood flow velocity using optical Doppler tomography," Opt. Lett. 22(14), 1119-1121(1997).

Chien et al., "12th International Conference on Cochlear Implants and Other Implantable Auditory Technologies," (2012).

Choma et al., "Sensitivity advantage of swept source and Fourier domain optical coherence tomography," Opt.Express 11, 7 (2003).

d. Boer et al., "Improved signal-to-noise ratio in spectral-domain compared with time-domain optical coherence tomography," Opt. Lett. 28, 3 (2003).

Dabbs, "Fiber-optic confocal microscope: FOCON," Appl. Opt. 31(16), 3030 (1992).

Duncan et al., "Processing algorithms for tracking speckle shifts in optical elastography of biological tissues, " J. Biomed. Opt. 6(4), 418-426(2001).

Fercher et al., "Measurement of intraocular distances by backscattering spectral interferometry," Opt. Commun. 17, 6 (1995).

Ford et al., "Fibre imaging bundles for full-field optical coherence tomography," Measurement Science and Technology, 2007, vol. 18, pp. 2949-2957.

Fujimoto, Daniel L. Farkas, Biomedical Optical Imaging, Oxford University Press, Inc. 198 Madison Avenue, New York, New York 10016 (2009).

Goebel et al., "Miniaturized two-photon microscope based on a flexible coherent fiber bundle and a gradient-index lens objective," Opt. Lett. 29, 2521-2523 (2004).

Gmitro, and D. Aziz, "Confocal microscopy through a fiber-optic imaging bundle," Opt. Let. 18, 565(1993).

Ha et al., "Compensation of motion artifacts in catheter-based optical frequency domain imaging," Opt. Express 18(11), 11418-11427 (2010).

Han et al., "Handheld forward-imaging needle endoscope for ophthalmic optical coherence tomography inspection, " J. Biomed. Opt. 13(2), 020505(2008).

Han et al., "Pixelation effect removal from fiber bundle probe based optical coherence tomography imaging," Opt. Express. 18, 7427-7439 (2010).

Han et al., "Common path optical coherence tomography with fibre bundle probe," Electron. Lett. 45(22), 1110-1112 (2009).

Hillman et al., "Common approach for compensation of axial motion artifacts in swept-source OCT and dispersion in Fourier-domain OCT," Optics Express, 2012.

Huang et al., "Motion compensated fiber-optic confocal microscope based on a common-path optical coherence tomography distance sensor," Opt. Eng. 50(8), 083201 (2011).

Huang et al., "Noncontact common-path Fourier domain optical coherence tomography method for in vitro intraocular lens power measurement", J. Biomed. Opt. 16(12), 126005(2011).

Huang et al., "Optical coherence tomography," Science, vol. 254, pp. 1178-1181, 1991.

Huang et al., "Real-time 3D and 4D Fourier domain Doppler optical coherence tomography based on dual graphics processing units," Biomed. Opt. Express 3(9), 2162-2174 ( 2012).

Huang et al., "Motion-compensated hand-held common-path Fourier-domain optical coherence tomography probe for image-guided intervention," Biomed. Opt. Express, vol. 3, Iss. 12, pp. 3105-3118 (2012).

Huber et al., "Buffered Fourier domain mode locking: unidirectional swept laser sources for optical coherence tomography imaging at 370,000 lines/s," Opt. Lett., vol. 31, pp. 2975-2977, 2006.

Huo et al., "Forward-viewing resonant fiber-optic scanning endoscope of appropriate scanning speed for 3D OCT imaging," Opt. Express 18(14),14375-14384(2010).

Iftimia et al., "Adaptive ranging for optical coherence tomography," Opt. Express 12(17), 4025-4034 (2004).

International Search Report and Written Opinion issued in International Application No. PCT/US2013/059736 dated Dec. 20, 2013.

International Search Report and Written Opinion issued in PCT Application No. PCT/US2013/053259 dated Aug. 1, 2013.

International Search Report and Written Opinion of PCT/US2012/036643.

International Search Report issued in PCT/US2011/044693 dated Mar. 20, 2012.

(56) References Cited

OTHER PUBLICATIONS

Jafri et al., "Optical coherence tomography guided neurosurgical procedures in small rodents," J. Neurosci. Methods 176(2), 85-89 (2009).
Jung et al. "Three-dimensional optical coherence tomography employing a 2-axis microelectromechanical scanning mirror," IEEE J. Sel. Top. Quantum Electron. 11(4), 806-810(2005).
Kang et al., "Endoscopic functional Fourier domain common path optical coherence tomography for microsurgery," IEEE J. Sel. Top. Quantum Electron. 16(4), 781-792(2010).
Kang et al., "Real-time three-dimensional Fourier-domain optical coherence tomography video image guided microsurgeries," J. Biomed. Opt. 17(8), 081403 (2012).
Kim et al., "Enhancement of common-path fourierdomain optical coherence tomography using active surface tracking algorithm," Transcations of the Korean Institute, 2012 (Abstract).
Kim et al., "Advanced Confocal Microscope Using Single Hollow-Core Photonic Bandgap Fibre Design," IEEE Electron. Lett., vol. 43(11) 608-609(2007).
Kim et al., "Fiber-Optic Confocal Microscopy Using a 1.55 μm Fiber Laser for Multimodal Biophotonics Applications," Journal of Special Topics in Quantum Electronics, vol. 14(1), 82-87(2008).
Klein et al., "Megahertz OCT for ultrawide-field retinal imaging with a 1050nm Fourier domain mode-locked laser," Opt. Express, vol. 19, pp. 3044-3062, 2011.
Knittel et al., "Endoscope-compatible confocal microscope using a gradient index-lens system," Opt. Comm. 188, 267-273 (2001).
Lee et al., "Motion correction for phase-resolved dynamic optical coherence tomography imaging of rodent cerebral cortex, " Opt. Express 19(22), 21258-21270 (2012).
Leitgeb et al., "Ultrahigh resolution Fourier domain optical coherence tomography," Opt. Express 12(10), 2156-2165(2004).
Leitgeb et al., "Performance of fourier domain vs. time domain optical coherence tomography," Opt.Express 11, 6 (2003).
Li et al., "Intraluminal fiber-optic Doppler imaging catheter for structural and functional optical coherence tomography," Opt.Lett. 26, 3 (2001).
Liang et al., "Intravascular atherosclerotic imaging with combined fluorescence and optical coherence tomography probe based on a double-clad fiber combiner," J.Biomed. Opt. 17, 3 (2012).
Liang et al., "Fiber confocal reflectance microscope (FCRM) for in-vivo imaging," Opt. Express. 9, 821-830 (2001).
Liu et al., "Optimization of an angled fiber probe for common-path optical coherence tomography," Opt. Letts., vol. 38, Issue 15, pp. 2660-2662 (2013).
Liu et al., "Distortion-free freehand-scanning OCT implemented with real-time scanning speed variance correction," Opt. Express 20(15), 16567-16583 (2012).
Maguluri et al., "Three dimensional tracking for volumetric spectral-domain optical coherence tomography," Opt. Express 15(25), 16808-16817 ( 2007).
Mao et al., "Graded-index fiber lens proposed for ultrasmall probes used in biomedical imaging," Appl. Opt 46, 8 (2008).
Mitragotri, "Current status and future prospects of needle-free liquid jet injectors," Nature Rev. Drug Discov. 5, 6 (2006).
Oh et al., ">400 kHz repetition rate wavelength-swept laser and application to high-speed optical frequency domain imaging," Opt. Lett., vol. 35, pp. 2919-2921, 2010.
Pepperkok, C. Schneider, L. Philipson, and W. Ansorge, "Single cell assay with an automated capillary injection system," Exp.Cell.Res. 17, 8 (1988).
Potsaid et al., "Ultrahigh speed 1050nm swept source / Fourier domain OCT retinal and anterior segment imaging at 100,000 to 400,000 axial scans per second," Opt. Express, vol. 18, pp. 20029-20048, 2010.
Potsaid et al., "Ultrahigh speed Spectral / Fourier domain OCT ophthalmic imaging at 70,000 to 312,500 axial scans per second," Opt. Express, vol. 16, pp. 15149-15169, 2008.
Cucu et al., "Active axial eye motion tracking by extended range, closed loop OPD-locked white light interferometer for combined confocal/en face optical coherence tomography imaging of the human eye fundus in vivo," Proc. of SPIE-OSA Biomedical Optics, SPIE vol. 7372, 73721R (2009).
Singh et al., "Physiological tremor during retinal microsurgery," Proc. 28th Annual Conf. IEEE Eng. Med. Bio. Soc.,171-172(2002).
Song et al., "Fiber-optic OCT sensor guided "Smart" micro-forceps for microsurgery," Biomedical Optics Express vol. 4, Iss. 7, pp. 1045-1050 (2013).
Song et al., "Ball Lens Fiber Optic Sensor based Smart Handheld Microsurgical Instrument," Proc SPIE. Mar. 20, 2013;8576.
Song et al., "Active Tremor Cancellation by A "Smart" Handheld Vitreoretinal Microsurgical Tool using Swept Source Optical Coherence Tomography," Optics Express, vol. 20, No. 21, pp. 23414-23421, Oct. 2012.
Stifter et al., "Polarisation-sensitive optical coherence tomography for material characterization and testing," Insight-Non-Destructing Testing and Condition Monitoring, 47, 209-212(2005).
Tan et al., "In-fiber common-path optical coherence tomography using a conical-tip fiber," Opt. Express 17(4),2375-2380(2009).
Tearney et al., "Scanning single-mode fiber optic catheter-endoscope for optical coherence tomography," Opt.Lett. 21, 3 (1996).
Tearney et al., "In vivo endoscopic optical biopsy with optical coherence tomography," Science 276, 3 (1997).
Vakhtin et al., "Common-path interferometer for frequency-domain optical coherence tomography," App. Opt. 42(34), 6935-6958 (2003).
Wieser et al., "Multi-Megahertz OCT: High quality 3D imaging at 20 million A-scans and 4.5 GVoxels per second," Opt. Express, vol. 18, pp. 14685-14704, 2010.
Xie et al., "Endoscopic optical coherence tomographic imaging with a CMOS-MEMS micromirror," Sensors and Actuators A, 2003, vol. 103, pp. 237-241.
Xie et al., "Fiber-optic-bundle-based optical coherence tomography," Opt. Lett. 30, 1803-1805 (2005).
Yamanari et al., "Full-range polarization-sensitive swept-source optical coherence tomography by simultaneous transversal and spectral modulation," Opt.Express 18, 17 (2010).
Yamanari et al., "Fiber-based polarization-sensitive Fourier domain optical coherence tomography using B-scan-oriented polarization modulation method," Opt. Express 14, 6502 (2006).
Yang et al., "Interstitial Doppler optical coherence tomography," Opt.Lett. 30, 3 (2005).
Yun et al., "High-speed optical frequency-domain imaging," Opt. Express 11, 11 (2003).
Zhang et al., "A common-path optical coherence tomography distance-sensor based surface tracking and motion compensation handheld microsurgical tool," Progress in Biomedical Optics and Imaging, 2011.
Zhang et al., "A surface topology for microsurgery guidance and intervention based on common-path optical coherence tomography," IEEE Trans. on Biomed. Eng. 56(9),2318-2321(2009).
Zhang et al., "Common-path low-coherence interferometry fiber-optic sensor guided micro-incision," J. Biomed. Opt. 16(9),095003(2011).
Zhang et al., "Graphics processing unit accelerated non-uniform fast fourier transform for ultrahigh-speed, real-time fourier-domain OCT," Optics Express, vol. 18, pp. 23472-23487.
Zhang et al., "Noninvasive volumetric quality evaluation of post-surgical clear corneal incision via high-resolution Fourier-domain optical coherence tomography," Electron. Lett., 46(22), 1482-1483(2010).
Zhang et al., "Real-time intraoperative 4D full-range FD-OCT based on the dual graphics processing units architecture for microsurgery guidance," Biomed. Opt. Express. 2(4), 764-770 (2011).
Zhang et al., "A Fiber-Optic Nerve Stimulation Probe Integrated with a Precise Common-Path Optical Coherence Tomography Distance Sensor," in OSA CLEO/IQEC 2010, CTuP2. http://www.opticsinfobase.org/abstract.cfrn?URI=CLE0-2010-CTuP2.
Zhang et al., "Real-time 4D signal processing and visualization using graphics processing unit on a regular nonlinear-k Fourier-domain OCT system." Opt. Express, 18(11), 11772-11784 (2010).
Zhang et al., "A Free-Hand Surface Tracking and Motion Compensation Microsurgical Tool System based on Common-path Optical (56) References Cited

OTHER PUBLICATIONS

Coherence Tomography Distance Sensor," in Conference on Lasers and Electro-Optics, OSA Technical Digest (CD) (Optical Society of America, 2010), paper CTuB6. http://www.opticsinfobase.org/abstract.cfm?uri-CLE0-2010-CTuB6.

Zhao et al., "Single camera sequential scan based polarization sensitive SDOCT for retinal imaging," Opt.Lett. 34, 3 (2009).

Zhao et al., "3D refraction correction and extraction of clinical parameters from spectral domain optical coherence tomography of the cornea," Opt.Express 18, 14 (2010).

Zhao et al., "Sensing and three-dimnesional OCT imaging of the cochlea and temporal bone: image-guided cochlear implantation," Proceediungs of SPIE, Mar. 2013, vol. 8565, pp. 1-7.

Zhao et al., "Sapphire ball lens-based fiber probe for common-path optical coherence tomography and its applications in corneal and retinal imaging," Opt.Lett. 37, 3 (2012).

Zhu et al., "Design and validation of an angle-resolved low-coherence interferometry fiber probe for in vivo clinical measurements of depth-resolved nuclear morphology," J.Biomed. Opt. 16(2011).

Zysk et al. "Optical coherence tomography: a review of clinical development from bench to bedside," J. Biomed. Opt. 12(5), 051403 (2007).

International Search Report and Written Opinion dated Jun. 29, 2015, issued in International Application No. PCT/US2015/026211.

\* cited by examiner

FIG. 12

FIBER OPTIC DISTAL SENSOR CONTROLLED MICRO-MANIPULATION SYSTEMS AND METHODS

STATEMENT OF GOVERNMENT SUPPORT

This invention was made with government support under Grant No. R01 EY021540, awarded by the National Institutes of Health National Eye Institute. The Government has certain rights in this invention.

TECHNICAL FIELD

The field of the currently claimed embodiments of this invention relates to motion-compensated micro-manipulation systems and methods of using the same, and more particularly systems and methods using optical coherence tomography with a motion-compensated micro-manipulation systems, including surgical blades.

BACKGROUND

Optical coherence tomography (OCT) has been viewed as an "optical analogy" of ultrasound sonogram (US) imaging since its invention in early 1990's. Compared to the conventional image-guided interventions (IGI) using modalities such as magnetic resonance imaging (MRI), X-ray computed tomography (CT) and ultrasound (US), OCT has much higher spatial resolution and therefore possesses great potential for applications in a wide range of microsurgeries, such as vitreo-retinal surgery, neurological surgery, otolaryngologic surgery and cochlear implantation. It has recently been demonstrated that OCT can be highly effective in freehand or robotically assisted retinal imaging or cochlear implantation, for example. A single-mode fiber can be lensed with state-of-the-art micro-optics to form a light beam with a spot size around 11 μm to 18 μm in retinal imaging, gastrointestinal endoscopy, coronary artery imaging, and needle-based Doppler OCT. Thus, OCT fiber optic sensing and imaging are becoming powerful tools for non-destructive cross-sectional imaging of biological tissues.

Retinal surgery is one example of microsurgery. In current practice, retinal surgery is performed under an operating microscope with free-hand instrumentation. Human limitations include an inability to clearly view surgical targets, physiological hand tremor, and lack of tactile feedback in tool-to-tissue interactions. In addition, tool limitations, such as lack of proximity sensing or smart functions, are important factors that contribute to surgical risk and reduce the likelihood of achieving surgical goals. Current instruments do not provide physiological or even basic interpretive information. Surgical outcomes (both success and failure) are limited, in part, by technical hurdles that cannot be overcome by conventional instrumentation.

Surgical blades are one type of hand-held surgical instrument. A hand-held instrument has the following advantages. First, it is small and lightweight, making it easy to access tight spaces. Second, surgeons are intimately familiar with hand-held instruments which can leverage the surgeons' experience and skills with little training Third, a small hand-held instrument offers greater safety because the surgeon can more easily override or remove the instrument in cases of malfunction.

A hand-held instrument, however, poses additional challenges over mechanically-rigid instruments. An operator of the hand-held instrument may be require control a tool tip of the instrument within very small tolerances, including sub-millimeter scale. For example, in some applications, surgical blades may need to be controlled at the sub-millimeter or micron scale. A surgeon may be required to perform a cut with a surgical blade that achieves a high level of accuracy with regard to the depth of the cut or it may be desirable to perform a cut that has a substantially even depth across a length of the cut. However, hand tremor, or physiological motion (e.g., the breathing and/or heartbeat, as well as volitional movement of the surgeon and/or patient) can make accurate and/controlled cuts or other micro-manipulations difficult to achieve and may cause damage to surrounding delicate tissues or cause localized hemorrhage or other injury and pose a high risk to the safety of the patient during performance of the procedure. The resulting involuntary changes in relative distance between the blade or other tool tip and the surgical tissue surface, although usually on the order of a few hundreds of micrometer at less than 5 Hz, may cause serious error due to the scale of microsurgery. Currently, no hand held surgical blade system can satisfy all of the above challenges during performance of a cutting operation. There remains a need for improved micro-manipulation systems and methods for surgical or microsurgical applications.

SUMMARY

A motion-compensated cutting system according to an embodiment includes a tool body having a size and configuration to be used for hand-held operation. The system also includes an actuator that is connected to the tool body and that has a shaft that is movable relative to the tool body. The system further includes a cutting implement attached to the shaft such that a distal end of the cutting implement is movable relative to the tool body in an axial direction. The system includes an optical coherence tomography system and a control unit. The optical coherence tomography system includes an optical fiber with a distal end fixed relative to the distal end of the cutting implement. The control unit is in communication with the optical coherence tomography system and the actuator, and is able to determine a position of the distal end of the cutting implement relative to a reference surface based on a signal received from the optical coherence tomography system. The control unit is also able to control the actuator to move the cutting implement to compensate for relative motion between the tool body and the reference surface at least during a cutting operation. The control unit is further able to maintain a predetermined depth of the distal end of the cutting implement with respect to the reference surface during the cutting operation.

According to an embodiment, a motion-compensated micro-manipulation system is provided. The micro-manipulation system includes a tool body with a size and configuration to be used for manual manipulation. The system also includes an actuator that is connected to the tool body and that has a shaft that is movable relative to the tool body. The system further includes a tool element attached to the shaft such that a distal end of the tool element is movable relative to the tool body in an axial direction. A position sensor is attached to the tool body and is able to detect a position of the shaft. Additionally, the system includes an optical coherence tomography system and a control unit. The optical coherence tomography system includes an optical fiber with a distal end fixed relative to the distal end of the tool element. The control unit is in communication with the optical coherence tomography system and the actuator, and is also in communication with the position sensor. The control unit is able to move the shaft, at a predetermined stage of a micro-manipulation procedure, to a reset position using input from the position sensor. Additionally or alternatively, the control unit is able to communicate a warning signal when the shaft is in a predetermined position. The control unit is further able to determine a position of the distal end of the tool element relative to a reference surface based on a signal received from the optical coherence tomography system, and to control the actuator to move the tool element to compensate for relative motion between the tool body and the reference surface.

According to an embodiment, a method of performing a motion-compensated cutting operation is provided. The method includes providing a cutting tool including a tool body and a cutting implement coupled to the tool body. The cutting implement has a distal end able to cut tissue of a patient. The method also includes providing an optical coherence tomography system, at least a portion of which is coupled to the cutting tool. The optical coherence tomography system includes an optical fiber with a distal end fixed relative to the distal end of the cutting implement. The method further includes performing the cutting operation, and controlling a position of the cutting implement along a longitudinal axis of the cutting implement over a duration of the cutting operation based on an input from the optical coherence tomography system to perform a cut of a desired depth.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated. All references cited in this specification are incorporated herein by reference.

The term "light" as used herein is intended to have a broad meaning that can include both visible and non-visible regions of the electromagnetic spectrum. For example, visible, near infrared, infrared and ultraviolet light are all considered as being within the broad definition of the term "light."

The term "real-time" is intended to mean that the OCT images can be provided to the user during use of the OCT system. In other words, any noticeable time delay between detection and image display to a user is sufficiently short for the particular application at hand. In some cases, the time delay can be so short as to be unnoticeable by a user.

The embodiments of the current invention that are described herein are not intended to be limited to the examples and terminology described. The following applications may contain features and examples that are contemplated as aspects of embodiments of the current invention: U.S. patent application Ser. No. 13/811,077, filed Jan. 18, 2013, which is a U.S. National Stage entry of PCT Application No. PCT/US2011/044693, filed Jul. 20, 2011, which claims priority to U.S. Provisional Application No. 61/365, 998, filed Jul. 20, 2010; U.S. patent application Ser. No. 14/114,885, filed Oct. 30, 2013, which is a U.S. National Stage entry of PCT Application No. PCT/US2012/036643, filed May 4, 2012, which claims priority to U.S. Provisional Application No. 61/482,300, filed May 4, 2011; U.S. patent application Ser. No. 13/957,145, filed Aug. 1, 2013, which claims priority to U.S. Provisional Application No. 61/678, 397, filed Aug. 1, 2012; PCT Application No. PCT/US2013/ 059736, filed Sep. 13, 2013, which is a continuation of U.S. patent application Ser. No. 13/618,810, filed Sep. 14, 2012; and U.S. patent application Ser. No. 14/163,491, filed Jan. 24, 2014. These references are hereby incorporated by reference in their entirety.

Some embodiments of the current invention provide a motion-compensated micro-manipulation system. According to some embodiments, the micro-manipulation system may be a cutting system, used as a surgical blade, for example, that enables high-precision cutting control. However, embodiments discussed herein include micro-manipulation systems in general, including embodiments of a cutting system. It is understood that embodiments of the current invention are not limited to those discussed herein, and may include other types of micro-manipulation systems including, for example, injectors, forceps, probes, and other surgical or micro-surgical instruments. The micro-manipulation system may include a tool body and an actuator connected to the tool body. The tool body can have a size, shape, and configuration to be used for manual manipulation. For example, the tool body can be handheld and may include a grip. The actuator can include a shaft or some other component that is movable relative to the tool body. In some embodiments, the actuator includes a PZT motor the moves the shaft in an axial direction. A tool element can be attached to the shaft such that a distal end of the tool element also is movable relative to the tool body. For example, when attached to the shaft, the tool element may be movable in an axial direction of the tool element. The system may further include an optical coherence tomography (OCT) system. The OCT system can include an optical fiber with a distal end that is fixed relative to the distal end of the tool element. The OCT system may also include an optical sensor that can receive a signal from the optical fiber.

The system may further include a control unit that is in communication with the OCT system and the actuator such that the control unit can send and/or receive signals between it and the OCT system and the actuator. The control unit may be able to determine a position of the distal end of the tool element relative to a reference surface based on a signal received from the OCT system. Further, the control unit may be able to control the actuator to move the tool element to compensate for relative motion between the tool body and the reference surface.

The reference surface may be a part of the subject of the micro-manipulation being performed. For example, in micro-surgical applications, the reference surface may be a tissue surface, including external and internal tissue surfaces, or subsurface structures in the tissue. However, the reference surface is not limited to tissue. According to some embodiments, micro-manipulation may be performed on subjects other than living organisms, in which case the reference surface can be any surface whose position is relevant to the micro-manipulation being performed.

The operation of some motion-compensation devices can be limited by the range of motion of the drive system used to perform the motion compensation. For example, a movable component of a drive system may start at an initial position, but the sum of movements performed during motion compensation may result in the movable component moving, on average, in one direction until the movable component reaches the limit of its range of motion. After reaching that limit in that direction, the movable component will not be able to move further in that direction, and thus motion compensation will be negatively impacted. However, according to some embodiments of the present invention, improvements are made to decrease the chance and/or negative consequences from the limited range of motion of a motion-compensation device.

For example, in some embodiments, a position sensor can be incorporated into or attached to the tool body to detect a position of the shaft. Signals from the position sensor can be received by the control unit, thus allowing the position of the shaft to be known to the control unit. Based on a signal received by the control unit from the position sensor or from a user-operable input, the control unit may cause the shaft to be moved to a reset position under certain circumstances. The reset position may be substantially at the center of a range of motion of the shaft, or some other position that provides sufficient freedom of motion of the shaft during motion compensation. For example, the control unit may move the shaft to the reset position at a predetermined stage of a micro-manipulation procedure being performed. The micro-manipulation system may also include a manually operable control in communication with the control unit so that an operator of the micro-manipulation system can use the control to signal the predetermined stage to the control unit. For example, the micro-manipulation system may include a button, switch, dial, or other input by which the operator of the system may reset the position of the shaft. The operator may choose to reset the position of the shaft between micro-manipulation operations where motion compensation has been in use. In this way, the shaft may start from the reset position for subsequent micro-manipulation operations. Accordingly, it is possible to avoid the situation where a micro-manipulation is started with the shaft already at or near the limit of its range of motion, and thus the odds of the shaft reaching the limit of its range of motion may be decreased.

In some embodiments, the position sensor may be an optical coherence tomography-based encoder. However, the position sensor is not limited to an OCT-based encoder, and may be another type of optical or electromagnetic encoder, or other some other type of position sensor known by those skilled in the art. In the case of an OCT-based encoder, the OCT-based encoder may use some common components with the OCT system to which the optical fiber is attached, or the OCT-based encoder may be separate from that OCT system.

According to some embodiments, the predetermined stage for resetting the shaft may be based on exceeding a predetermined distance between the distal end of the tool element and the reference surface. For example, after performing a micro-manipulation procedure, the operator of the system may withdraw the tool body of the system away from the subject of the micro-manipulation and thus away from the reference surface. This withdrawing of the tool body from the reference surface may be used to trigger an automatic resetting of the shaft position without necessarily requiring a manual activation of a user operable input to perform the reset. In some embodiments, the resetting of the shaft may be delayed by some amount of time after the predetermined distance is exceeded.

The control unit may communicate a warning signal when the shaft is in a predetermined position based on a position of the shaft as determined by the position sensor. For example, the predetermined position may be at or near a limit of a range of motion of the shaft. The micro-manipulation system can further include a warning device that receives the warning signal from the control unit based on a signal from the position sensor. In some embodiments, the warning device may communicate a visual or auditory warning to an operator of the micro-manipulation system. Thus, an operator of the micro-manipulation system can be warned when the shaft is at or near the limits of its range of motion and can then take appropriate action to prevent or mitigate undesirable consequences of the shaft reaching the limits of its range of motion. For example, the operator may choose to at least temporarily cease the procedure being performed, to reset the position of the shaft, or to adjust a position of the tool body.

According to embodiments of the present invention, the control unit may control the actuator to achieve a predetermined distance between the distal end of the tool element and the reference surface. The reference surface need not be distal to the distal end of the tool element. For example, if the distal end of the tool element is distal to the reference surface with respect to the tool body, then the predetermined distance may indicate a depth of the tool element in the reference surface.

In some embodiments, the tool element may be detachable from the shaft, and may also be disposable. The optical fiber may also be detachable from a remainder of the OCT system, and may also be disposable. The optical fiber can be pre-attached to the tool element so that the distal end of the optical fiber is fixed relative to the distal end of the tool element. The other end of the optical fiber may then be attachable to a remainder of the OCT system. In some embodiments, the tool element can be a cutting implement, such as a blade, pick, or saw. However, the tool element is not limited to a cutting implement, and may also include, for example, a needle (e.g., for performing injection), forceps, a probe, or other tools, including tools used in micro-surgery or other micro-manipulation applications.

According to some embodiments, a motion-compensated cutting system is provided. It is to be understood that features of the above embodiments may also be included in embodiments of the cutting system described herein, even where those features are not explicitly mentioned in the following descriptions of the cutting system embodiments. Correspondingly, features of embodiments of the cutting system described below may also be used in the above discussed embodiments of the micro-manipulation system, even where those features where not explicitly described in the above embodiments.

The cutting system may include a tool body having a size and configuration that allows for manual cutting with the cutting system. An actuator with a movable shaft can be connected to the tool body. A cutting implement attached to the shaft such that a distal end of the cutting implement is movable relative to the tool body in an axial direction of the cutting implement. An OCT system may be included with the cutting system, and at least a portion of the OCT system may be attached to the tool body and/or the cutting implement. An optical fiber of the OCT system has a distal end that is fixed relative to the distal end of the cutting implement. For example, the optical fiber may be attached to the cutting implement such that at least a portion of the optical fiber extends parallel to a portion of the cutting implement. In some embodiments, the OCT system uses common-path OCT. One or both of the cutting implement and the optical fiber may be detachable from a remainder of the motion-compensated cutting system.

A control unit in communication with the OCT system and the actuator can determine a position of the distal end of the cutting implement relative to a reference surface based on a signal received from the OCT system. The control unit can control the actuator to move the cutting implement to compensate for relative motion between the tool body and the reference surface at least during a cutting operation. Such relative motion could be caused by, for example, a hand tremor of the operator, or voluntary or involuntary motion of the reference surface or the operator.

According to some embodiments, the control unit can maintain a predetermined depth of the distal end of the cutting implement with respect to the reference surface during the cutting operation. For example, with the aid of the cutting system according to embodiments of the invention, the operator may perform a cut with a substantially constant depth. However, the control unit may also be able to control the depth of the cut such that the depth of the cut varies across the length of the cut. The variation in the depth of the cut may be preprogrammed or determined by the system during or prior to the cutting operation being performed. For example, the depth of the cut may be varied to cut or avoid cutting a structure, which may be detected by the OCT system.

During a cutting or other micro-manipulation operation, the subject of the operation may deform or move in response to the micro-manipulation tool being used. Accordingly, the control unit may also detect deformation of the subject of the cutting operation based on a signal from the OCT system. The deformation may result from movement of the subject, insertion of the cutting implement into the subject, or movement of the cutting implement along a length of a cut as a cutting operation is performed. Based on the detected deformation, the control unit can control the actuator to compensate for the deformation. In this way, the cutting operation can be performed according to desired criteria despite the deformation of the tissue.

According to some embodiments, the cutting system may have a position sensor attached to the tool body and arranged to detect a position of the shaft. The position of the shaft may be the position of a portion of the shaft relative to the position sensor, which can indicate the extent to which the shaft is extended from a motor or other portion of the actuator. Thus, the position sensor may be used to determine not only a current position of the shaft, but also how much room is left for the shaft to move in one or more directions. In some embodiments, the position sensor may be an encoder, including, for example, an optical coherence tomography-based encoder. However, other types of position sensors known in the art may also be used.

Using input from the position sensor, the control unit may control to actuator to move the shaft in certain ways. For example, the control unit can move the shaft to a reset position after a single cut is completed. In some embodiments, the control unit may communicate a warning signal when the shaft is at or near a limit of a range of motion of the shaft.

In some embodiments, the motion-compensated cutting system can include a measuring unit to measure a length of a cut performed by the cutting system. The measuring unit can be used in combination with the control unit and the actuator to control the position of the cutting implement as a function of the length of the cut. For example, the depth of the cut can be varied based on the length of the cut, or the cutting implement can be at least partially withdrawn after the cut reaches a certain length. In some embodiments, the measuring unit measures the length of the cut using speckle de-correlation. For example, speckle de-correlation can be used to determine a speed at which the optical fiber traverses the reference surface. This speed of the cutting operation can then be used to determine a distance by using a duration of the cutting operation.

Some embodiments of the current invention provide a method of performing a motion-compensated cutting operation. The method may include providing a cutting tool that has a tool body and a cutting implement attached to the tool body. A distal end of the cutting implement may be used to cut a surface, including tissue of a patient. The method also includes providing an optical coherence tomography (OCT) system having an optical fiber with a distal end fixed relative to the distal end of the cutting implement. The method further includes performing the cutting operation, and controlling a position of the cutting implement along a longitudinal axis of the cutting implement over a duration of the cutting operation. This controlling of the position is based on an input from the OCT system to perform a cut of a desired depth. The depth may be constant or variable over a length of the cut. In some embodiments, the method also includes controlling the position of the cutting implement to move the cutting implement in a repetitive back-and-forth motion along the longitudinal axis of the cutting implement. This type of control can be used to saw or puncture tissue.

In some embodiments, the control unit controls the actuator based on a closed-loop proportional-integral-derivative (PID) control algorithm. The control unit and the actuator may reduce or eliminate a change in the distance between the distal end of the optical fiber and the reference surface that would result from one or both of a motion of the reference surface and a motion of a hand of an operator of the tool body. The motion of the reference surface and the motion of the operator's hand may be voluntary or involuntary motion. The motion of the operator's hand may be, for example, a hand tremor of the operator. At the start of and during a micro-manipulation operation, the positioning of a tool element or cutting implement may be even harder to maintain for an operator without motion compensation. Accordingly, the control unit and the actuator may reduce or eliminate the change in the distance during the operation being performed. In some embodiments, the OCT system can monitor the position of the reference surface in real time.

Some of the embodiments of the current invention use a single fiber probe as a common-path optical coherence tomography (CP-OCT) distance sensor and a high-speed piezo-electric micro linear motor for one-dimensional actuation. The distance between the distal end of the tool element or cutting implement and the target surface may be determined from the OCT signal by, for example, an automatic edge-searching algorithm. The micro linear motor may be controlled by a computer, for example, according to feedback from the CP-OCT distance sensor.

In micro-surgery, a desired depth or position of the tool element within tissue may be known, and the tissue into which the tool element is inserted may include a variety of tissue layers and the tissue may be deformable. For example, the tissue may deform by a thickness of one or more layers changing when the tool element is inserted into or pressed against the material. The tissue may also deform by movement of the subject or the specific tissue itself. Accordingly, the optical detection system may detect deformation of the tissue resulting from at least one of movement of the tissue and movement of the tool element into or against the tissue. The control unit can control the actuator to compensate for the deformation of the tissue.

In some embodiments, the optical detection system uses common-path optical coherence tomography (CP-OCT). The optical fiber may include a bare single-mode fiber with a protective sheath. At least a portion of the single-mode fiber with the protective sheath may be parallel to a longitudinal axis of the tool element. In some embodiments, the tool element and/or the optical fiber may be detachable from a remainder of the motion-compensated micro-manipulation system. Accordingly, the tool element and the optical fiber may be disposable. The type of optical coherence tomography (OCT) on which the OCT system is based may be, for example, one of swept source or time encoded frequency domain OCT, spatial domain or Fourier transform OCT, and frequency domain OCT. The OCT system may perform an imaging of the tissue or other reference surface via OCT during one or more of before, during, and after performance of the micro-manipulation. The imaging during and after the micro-manipulation may include determining a result of the micro-manipulation, such as, for example, a depth or length of a cut achieved by a cutting operation.

The actuator of the micro-manipulation system according to some embodiments may include a lead zirconium titanate (PZT) motor and a rod to which the tool element is directly or indirectly fixed. The PZT motor can thus drive the rod to move the tool element. A user-operable mechanism or input may also be included for selectively turning on and off at least one of the actuator and the OCT system. "Turning on and off" may include, for example, controlling when the actuator is able to change the position of the tool element.

Some embodiments of the current invention can be integrated into standard freehand micro-surgical instruments and can enable surgeons to make precise micro-manipulations, such as cuts or incisions, safely and effectively.

The systems and methods described above may apply to micro-manipulations involving biological material, such as human tissue, but the systems and methods are not limited thereto. For example, the micro-manipulations may be for any object or system for which motion-compensated manipulation can be useful.

Figure 1:
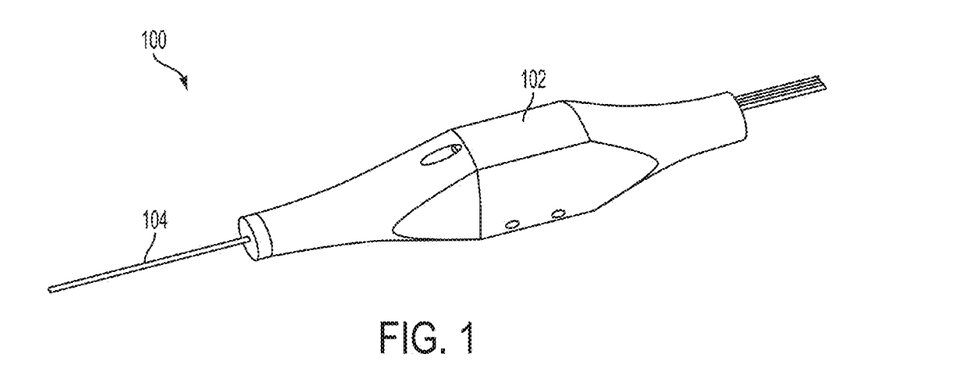
FIG. 1 shows a motion-compensated surgical blade system according to an embodiment of the current invention.
Figure 2:
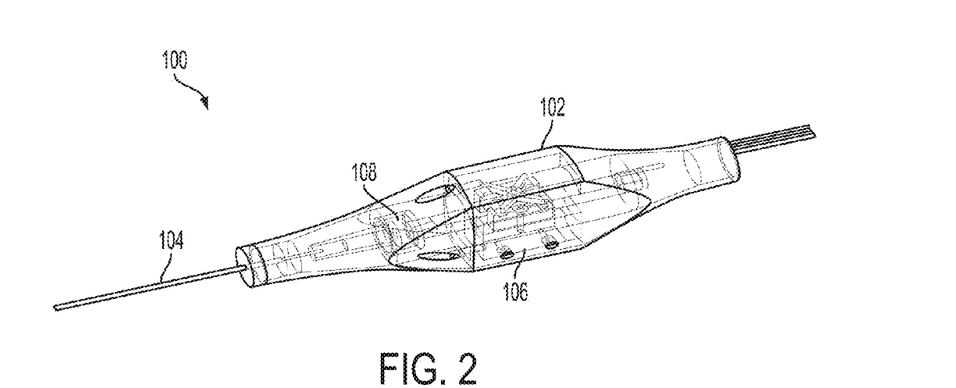
FIG. 2 shows a view into the interior of the motion-compensated blade system of FIG. 1 according to an embodiment of the current invention.
Figure 3:
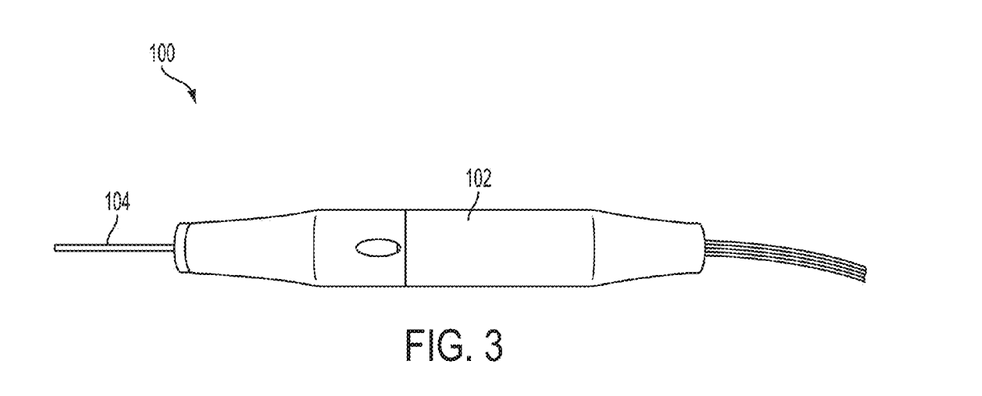
FIG. 3 shows an example of a motion-compensated surgical blade system according to an embodiment of the current invention.

FIGS. 1-3 show examples of a tool body and cutting implement of a motion-compensated cutting system according to an embodiment of the current invention. The motion-compensated cutting system 100 has a tool body 102 that has a size and shape allowing handheld use and manual control by an operator of the system. A cutting implement 104 is attached to an actuator made up of a shaft 108 and a motor 106. In some embodiments, the cutting implement 104 may be detachable from the shaft 108. Although FIGS. 1-3 shows an example of a cutting system, a motion-compensated system having a different tool element in place of the cutting implement 104 could be used with the tool body 102 shown in FIGS. 1-3. In these other embodiments, the control unit (not shown) may be programmed to achieve desired performance characteristics depending on the type of tool element in use and the specific micro-manipulation being performed.

Figure 4:
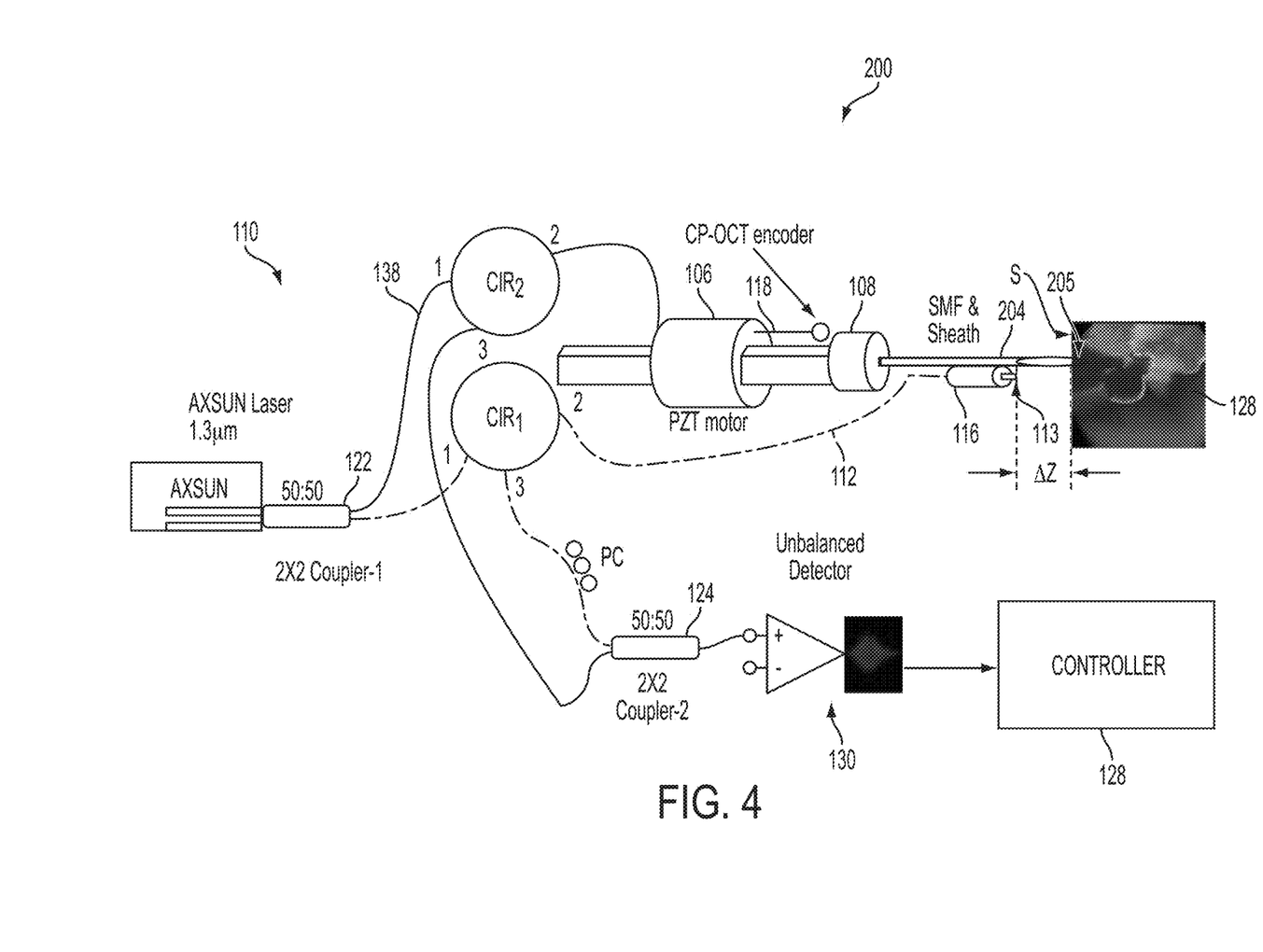
FIG. 4 shows a schematic view of a motion-compensated surgical blade system according to an embodiment of the current invention.

FIG. 4 shows a schematic of a motion-compensated micro-manipulation system according to an embodiment of the present invention. According to various embodiments, the micro-manipulation system 200 shown can be for the cutting system 100 shown in FIGS. 1-3, or some other micro-manipulation system. The micro-manipulation system 200 includes a tool element 204 attached to the shaft 108, which is actuated by the motor 106. An optical coherence tomography (OCT) system 110 is shown that includes an optical fiber 112 and an OCT source 114 (e.g., a laser). As one example, a laser having a 1.3 μm wavelength from AXSUN Technologies, Inc. has been used as the OCT source 114 in an embodiment. The optical fiber 112 has a distal end 113 that is a fixed distance from a distal end 205 of the tool element 204. A sheath 116 surrounds at least a portion of the optical fiber 112. Light from the OCT source 114 may be fed through a circulator $CIR_1$ (from port 1 to port 2) on the way to the distal end 113 of the optical fiber 112. A signal then returns from the sample 126 that is the subject being imaged or detected by the OCT system 110. The return signal may be fed through the circulator $CIR_2$ (from port 2 to port 3) on its way to a detector 130. The detector 130 may be, for example, an unbalanced detector. The OCT system 110 may also include a polarized controller PC and couplers 122, 124, as shown in FIG. 4. A signal from the detector 130 may then be transmitted to a controller 128. The controller 128 can send signals to the motor 106 via a wired or wireless connection. Based on the signal received from the OCT system 110, the controller may determine a distance ΔZ between the distal end 113 of the optical fiber 112 and the reference surface S. Correspondingly, because the distal end 113 of the optical fiber 112 is fixed relative to the distal end 205 of the tool element 204, the controller 128 may also determine a depth of or distance between the distal end 205 of the tool element 204 with respect to the subject 128. In this way, the controller 128 may determine a depth of a cut or incision made by a cutting implement, for example.

As shown in FIG. 4, the micro-manipulation system 200 may also include a position sensor 118. In some embodiments, the position sensor 118 can be an OCT-based encoder, or some other mechanical or electromagnetic encoder or other position sensor. The position sensor 118 can detect a position of the shaft 108. A signal from the position sensor 118 may then be transmitted to the controller 128 so that a position of the shaft 108 is known to the controller 128.

A micro-manipulation system according to embodiments of the invention can perform GPU signal processing and CPU data streaming in real time in order to perform real time control of the micro-manipulation system based on input from the OCT system.

In some of the embodiments described above and shown in the figures, the optical fiber 112 is attached to the cutting implement 104 or tool element 204. However, embodiments of the invention are not limited to such a configuration. For example, the optical fiber 112 may be mounted onto some portion of the tool body 102 or arranged in some other manner so as to be a fixed distance from the distal end 205 of the tool element 204.

According to some embodiments, the controller 128 may include, for example, a data processor, software, or a combination of hardware and software. The controller 128 can be a dedicated "hard-wired" device, or it can be a programmable device. For example, it can be, but is not limited to, a personal computer, a work station or any other suitable electronic device for the particular application. In some embodiments, it may be integrated into a unit or it could be attachable, remote, and/or distributed.

In some embodiments, the controller 128 is further configured to determine an amount, speed and/or direction of movement of the tool element 204 to be moved by the shaft 108 and motor 106 to counter motions of the distal end 205 of the tool element 204 relative to a reference surface S of the tissue or other object of the micro-manipulation.

In some embodiments, the OCT system 110 can have a light source comprising a superluminescent light emitting diode. In some embodiments, a spectrometer can be used as an optical detector of the OCT system 110. In other embodiments, the light source can be a wavelength swept laser and the optical detector can be a photodetector. The broad concepts of the current invention are not limited to these particular examples.

FIG. 4 shows a laser as the OCT source 114 for the OCT system 110, according to one embodiment of the present invention. The laser may be optically coupled to the optical fiber 112. As discussing above, an OCT signal can sent back through the optical fiber 112 from the tissue or other sample 126, and circulated through the circulator $CIR_1$ to the unbalanced detector 120, passing a polarized controller PC and a coupler 124. For example, the couplers 122, 124 can be 2×2 couplers, as shown in FIG. 1. The optical fiber 112 may provide a common transmit and receive optical path such that the OCT system is a common-path optical coherence tomography system (CP-OCT).

In addition, as shown in FIG. 4, a second optical fiber 138 can be coupled to the OCT source 114 for use with the position sensor 118, where the position sensor 118 is OCT-based. The signal from the position sensor 118 can be sent through a circulator $CIR_2$ on the signal's way from the OCT source 114 to the position sensor 118, and as the signal travels from the position sensor 118 to the unbalanced detector 130.

The following provides some examples according to some embodiments of the current invention. The general concepts of the current invention are not limited to these particular examples that are provided to explain concepts of the current invention.

EXAMPLES

The following examples relate to a micro-surgical blade integrated with a common-path swept-source optical coherence tomography (CP-SSOCT) based system for high-precision cutting control. In these examples, the blade was connected to a linear motion motor to provide an accurately and precisely controlled up and down cutting motion with accuracy on the order of 10 µm during freehand use. In this study, the cutting motion was controlled by a CP-SSOCT sensor driven PZT motor with a step resolution of <5 µm, which concurrently reduces the hand tremor transmitted to the tip of the instrument by the surgeon. The present embodiment uses a closed-loop proportional-integral-derivative (PID) control algorithm based on graphics processing unit (GPU) processing and an analysis rate of up to 500 Hz. A motion-compensated high-precision surgical blade using a fiber optic distal sensor to monitor, in real time, the relative position between the blade tip and the tissue surface was demonstrated. The linear motion motor controlled the blade tip position based on the OCT sensor input to rapidly compensate for unwanted tissue and hand motions providing precise control of the blade cutting depth and motion. The sensor-servo loop in the present example was capable of 500 Hz monitoring and blade position adjustments. Future embodiments may be capable of more rapid processing and instrument response.

The design of the system used in this example is shown in FIGS. 1-3. The examples in FIGS. 1-3 have a 12-degree beveled tip. However, the blade tip is not limited in size or shape. Additionally, the embodiment of this example used a piezoelectric motor (LEGS-L01S-11, PiezoMotor) and a commercial small gauge syringe needle (in the present prototype, 25-gauge or smaller or other microblade). A lure-lock hypodermic needle set-up was designed for easy replacement with the front holder and motor shaft. The piezoelectric motor used in this prototype had a maximum speed of 20 mm/s, maximum stroke of 55 mm, maximum force of 6.5 N, and a resolution of less than 1 nm. The front holder had enough inner space to allow the inner needle to move back and forth 12 mm. The tool's overall length was 108 mm excluding the surgical needle and weighed about 50 g, including the motor weight of 20 g.

Figure 5:
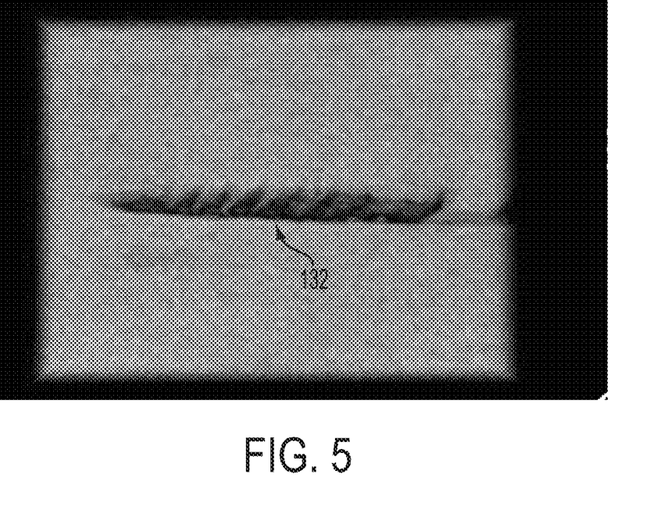
FIG. 5 shows an OCT image of an incision made by a motion-compensated surgical blade system according to an embodiment of the current invention.
Figure 6:
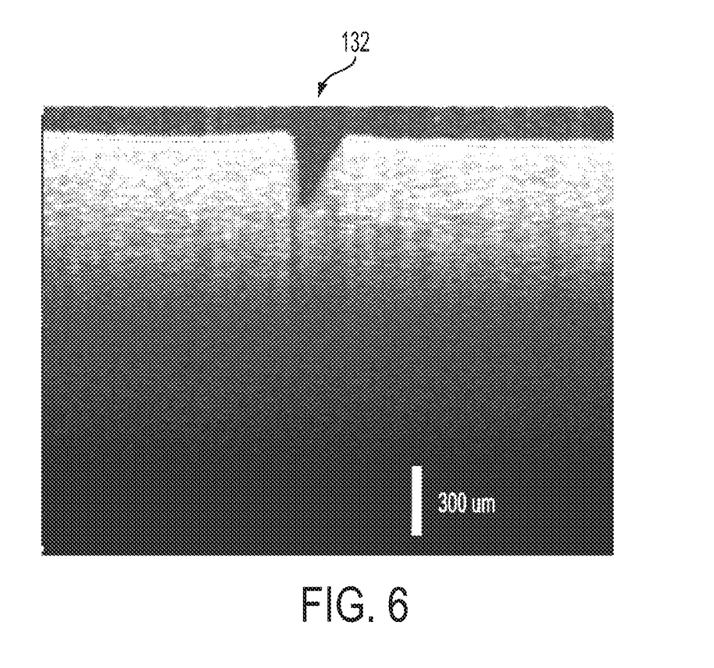
FIG. 6 shows an OCT cross-section image of the incision shown in FIG. 5.

The basic performance of the fiber optic sensor driven handheld microsurgical blade of this example was evaluated. FIGS. 5 and 6 show OCT images of a clean micro-incision site as performed by the smart blade. Specifically, FIG. 5 shows an OCT image of an incision 132 made by a motion-compensated cutting system according to an embodiment of the current invention. The field of view of the image is about 2 mm×2 mm. FIG. 6 shows a cross-sectional OCT image of an incision 132 made by the motion-compensated cutting system according to an embodiment, with a scale bar of 300 µm.

Figure 7:
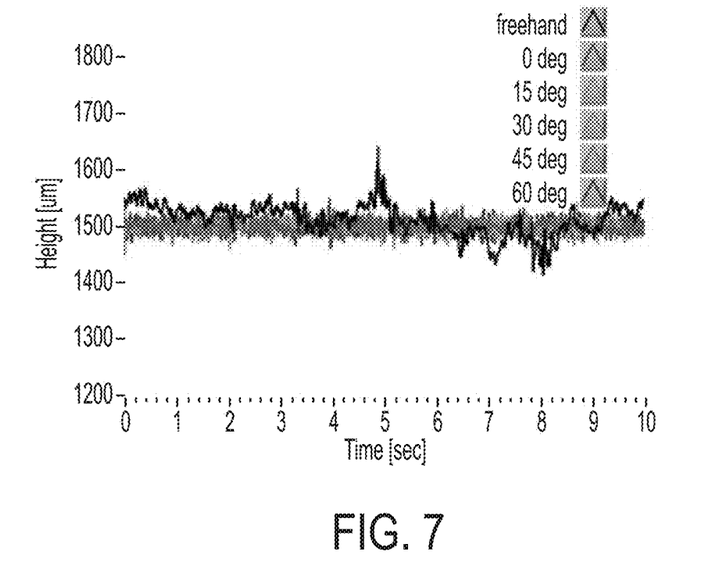
FIG. 7 shows a non-motion-compensated result and motion-compensated results of the cutting depth at different incision angles as an example according to an embodiment of the current invention.
Figure 8:
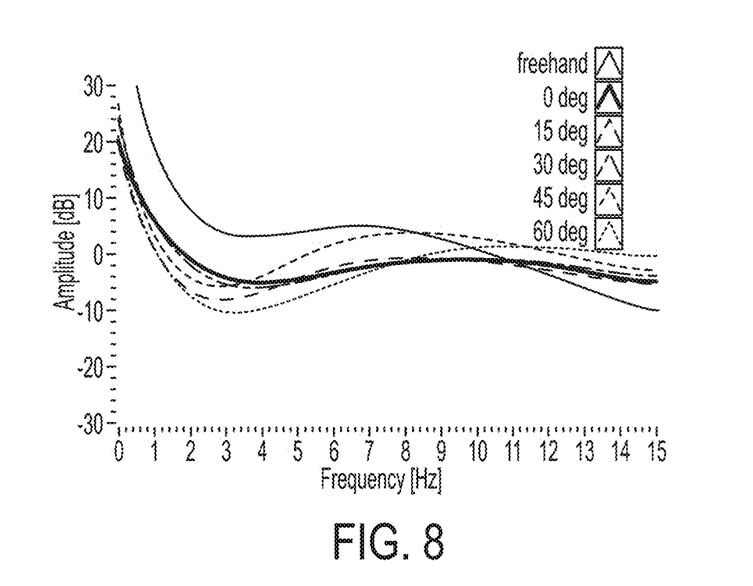
FIG. 8 shows a non-motion-compensated result and motion-compensated results of a Fourier analysis at different incision angles for an example according to an embodiment of the current invention.

FIGS. 7 and 8 compare freehand and compensated blade positions while cutting, and also their frequency analyses up to 15 Hz over a 10 second period, at different incision angles. The incision mode of the smart blade was assessed and its performance was analyzed by measuring the tool tip position using a dual fiber-optic OCT distance sensing scheme. The graph in FIG. 7 shows experimental data of the cutting depth according to a non-motion-compensated cutting operation and various motion-compensated operations of the cutting depth at different incision angles as an example according to an embodiment of the current invention. The angle is the angle at which the cutting implement is positioned with respect to the surface being cut. The graph in FIG. 8 shows results from a non-motion-compensated result and various motion-compensated results. The position of the cutting implement is shown using a Fourier analysis for operations performed at different incision angles and for the freehand example.

Figure 9:
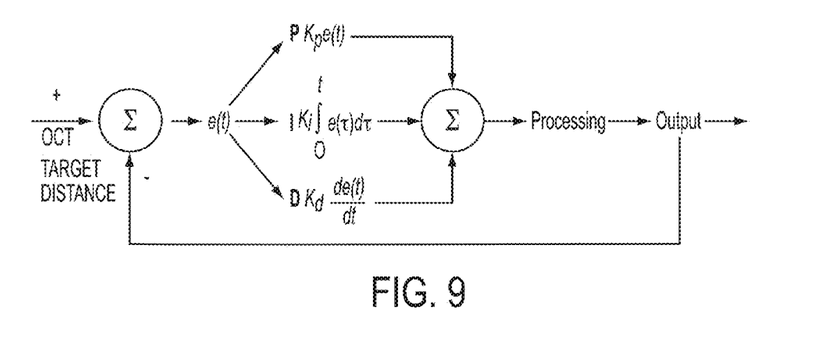
FIG. 9 shows an example of a control process of a motion-compensated surgical blade system according to an embodiment of the current invention.

FIG. 9 shows an example of a control process used in a motion-compensated cutting system according to an embodiment of the current invention. The PID control algorithm was employed to adaptively move the rod of the PZT motor that is connected to the cutting implement used for cutting tissue. The difference between a target position of the distal end of the cutting implement and the detected OCT peak is called error, e(t). The PZT motor controls the motion of cutting implement to compensate the error so as to consistently maintain the desired depth of the cutting implement. The control output of the PZT motor can be described by the following equation:

$$u(t) = K_p e(t) + K_i \int_0^t e(s)ds + K_d de(t)/dt \quad (1)$$

where $K_p$, $K_i$ and $K_d$ are the proportional gain, integral gain and derivative gain, respectively. The above parameters are adjusted based on experience and RSME. These parameters are different from the values obtained for active tracking in air space since the tissue damping effects have an impact on the performance of the PID controller. A block diagram of PID control for distance maintaining is illustrated in FIG. 4. The output is converted into the control voltage and compensation frequency of the PZT motor.

A distance between the tissue and optical fiber tip can be maintained by a real-time feedback PZT motor with a resolution of ~5 μm (or less than 5 μm), which also dramatically reduces hand tremor, using a closed-loop PID active control algorithm.

Figure 10:
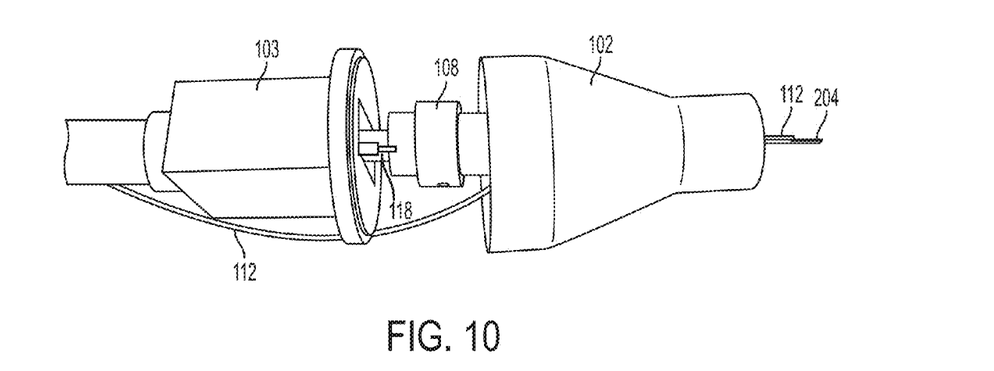
FIG. 10 shows a motion-compensated surgical blade system according to an embodiment of the current invention.
Figure 11:
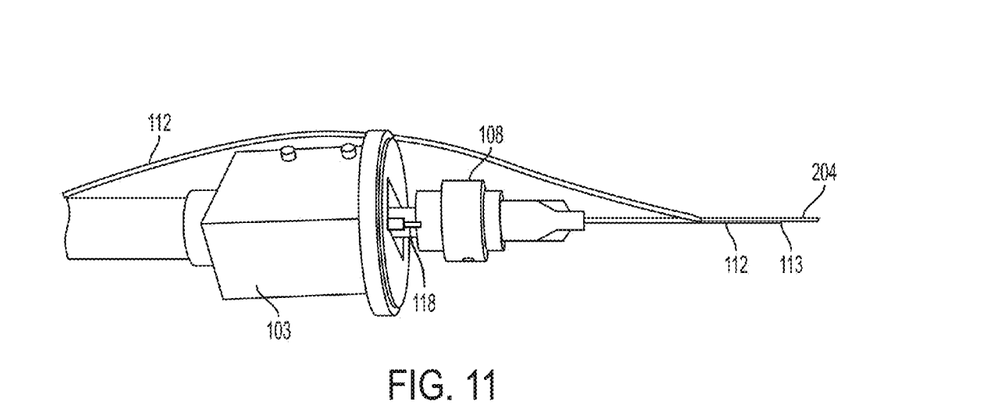
FIG. 11 shows another view of the motion-compensated surgical blade system shown in FIG. 10.

FIGS. 10 and 11 show close-up views of an example of a motion-compensated micro-manipulation system according to an embodiment of the current invention. In FIG. 10, the tool body includes two separate pieces 102, 103, with a space between 102 and 103 that shows the arrangement of the position sensor 118 and shaft 108. The optical fiber 112 is fed through a portion of the tool body 102 so that the distal end 113 of the optical fiber 112 emerges near the tool element 204. FIG. 11 shows the micro-manipulation system with the portion 102 of the tool body removed to expose the base of the tool element 204 and how it is connected to the shaft 108.

Figure 12:
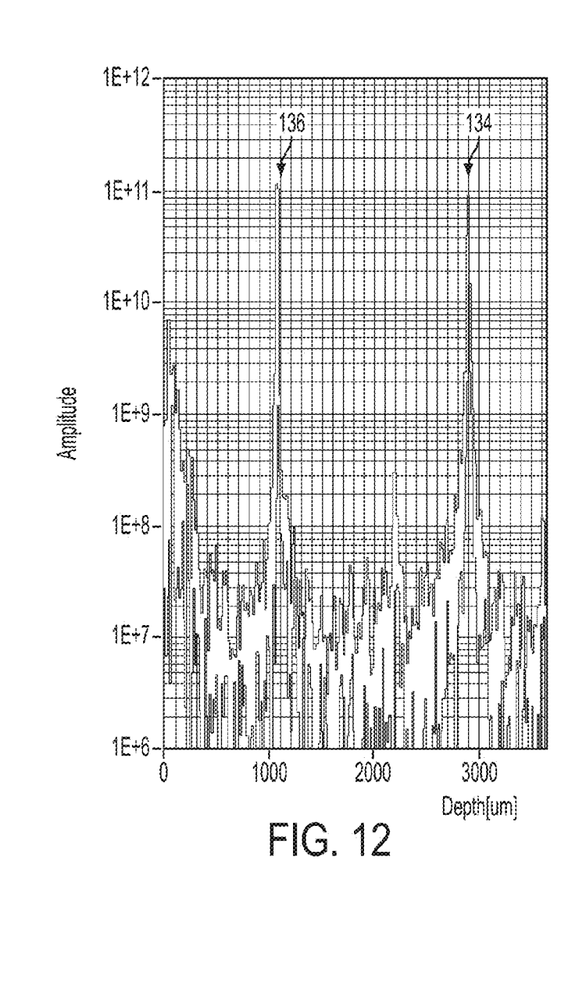
FIG. 12 shows a result of signals from two OCT sensors according to an embodiment of the current invention.

FIG. 12 shows a result of signals from an OCT-based position sensor and an OCT sensor connected to the optical fiber 112 that is fixed relative to the distal end of the tool implement 204 according to an embodiment. An offset can be seen between the signal 134 from the optical fiber 112 and the sensor 136 from the position sensor that detects the location of the shaft 108.

Figure 13:
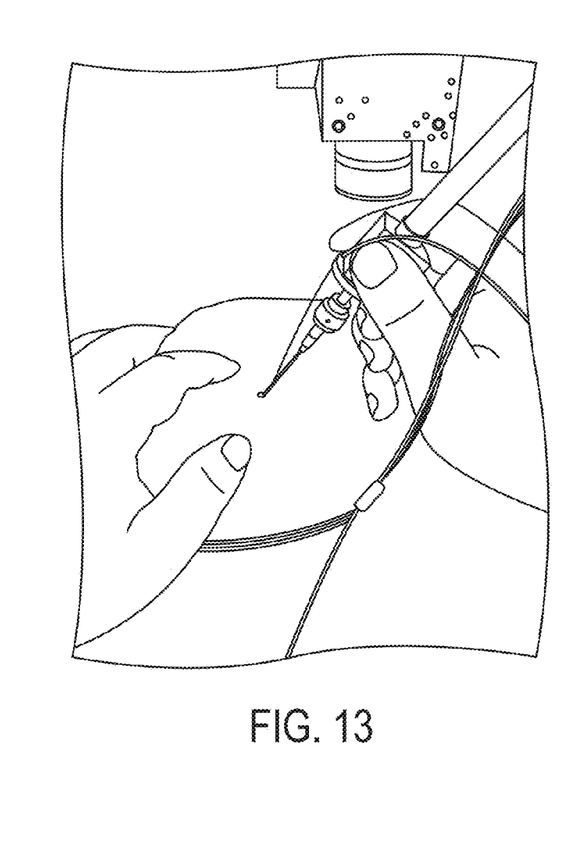
FIG. 13 shows an example of a motion-compensated surgical blade system being used by an operator according to an embodiment of the current invention.

FIG. 13 shows an example of an operator using a hand-held, motion-compensated cutting system according to an embodiment of the invention.

To detect the interface between tissue and air, an effective peak detection algorithm is critical to determining the peak position of the OCT A-line signal coming from the interface. The interferometric CP-SSOCT sensor signal at position Δz after Fourier transform can be described as follows:

$$I(2n\ \Delta z) = (\rho/2e) Sqrt(P_r P_s) R_s\ L(2n\ \Delta z) exp(i2k_0 n\ \delta z) \quad (2)$$

where n is the tissue refractive index, ρ is the detector responsivity, and e is the electronic charge. Pr and Ps are the reference and sample power, respectively. Rs is the sample reflection coefficient; L(2n Δz) is the normalized-amplitude mutual coherence function; the last term is phase related to central wave number k0, n and fractional imaging depth. The above equation shows that the OCT signal has a peak value at the air-tissue interface since Rs is at a maximum at this location. Simple maximum value peak detection works very well for dry phantoms or less scattering biological tissue. However, it introduces high root mean square error (RMSE) of 30~50 μm for wet or otherwise strong scattering biological tissue. To reduce the false alarm rate of peak detection caused by the random speckle noise in turbid media, the mass center of local peaks was calculated to suppress the impact of strong speckle signals scattering back from the deeper layers of the tissue. Here it was assumed that peak OCT signal is the interface between the tissue and air. This mass center algorithm significantly improves the performance for accurate peak detection with a root mean square (RMS) of 2~3 μm for still strongly scattering biological tissue with a performance enhancement at least 10 times that of the simple peak maximum value detection algorithm.

REFERENCES

1. Cheol Song, Dong Yong Park, Peter L. Gehlbach, Seong Jin Park, and Jin U. Kang, "Fiber-optic OCT sensor guided "SMART" micro-forceps for microsurgery," Biomedical Optics Express Vol.4, Iss. 7, pp. 1045-1050 (2013)

2. Xuan Liu and Jin U. Kang, "Optimization of an angled fiber probe for common-path optical coherence tomography," Opt. Letts., Vol. 38, Issue 15, pp. 2660-2662 (2013).

3. Cheol Song, Peter L Gehlbach, Jin U Kang. Ball Lens Fiber Optic Sensor based Smart Handheld Microsurgical Instrument. Proc SPIE. 2013 Mar 20;8576.

4. Mingtao Zhao, Yong Huang, and Jin U Kang, "Sapphire ball lens based fiber probe for common-path optical coherence tomography and its applications in corneal and retinal imaging," Optics Letters Vol. 37, Iss. 23, pp. 4835-4837 (2012)

5. Yong Huang, Xuan Liu, Cheol Song, and Jin U. Kang, "Motion-compensated hand-held common-path Fourier-domain optical coherence tomography probe for image-guided intervention," Biomed. Opt. Express, Vol. 3, Iss. 12, pp. 3105-3118 (2012)

6. Cheol Song, Peter L. Gehlbach, and Jin U. Kang, "Active Tremor Cancellation by A "Smart" Handheld Vitreoretinal Microsurgical Tool using Swept Source Optical Coherence Tomography," Optics Express, Vol. 20, No. 21, pp. 23414-23421, October 2012

7. Jin U. Kang, Peter Gehlbach, Russell H. Taylor, Kang Zhang, "Surface Tracking and Motion Compensating Surgical Tool System," WO Patent WO/2012/012,540, Jan. 26, 2012

8. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science 254, 4 (1991).

9. A. F. Fercher, C. K. Hitzenberger, G. Kamp, and S. Y. El-Zaiat, "Measurement of intraocular distances by backscattering spectral interferometry," Opt. Commun. 17, 6 (1995).

10. R. Leitgeb, C. K. Hitzenberger, and A. F. Fercher, "Performance of fourier domain vs. time domain optical coherence tomography," Opt. Express 11, 6 (2003).

11. J. F. d. Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 3 (2003).

12. M. A. Choma, M. V. Sarunic, C. Yang, and J. A. Izatt, "Sensitivity advantage of swept source and Fourier domain optical coherence tomography," Opt. Express 11, 7 (2003).

13. M. Yamanari, S. Makita, V. D. Madjarova, T. Yatagai, and Y. Yasuno, "Fiber-based polarization-sensitive Fourier domain optical coherence tomography using B-scan-oriented polarization modulation method," Opt. Express 14, 6502 (2006).

14. M. Zhao and J. A. Izatt, "Single camera sequential scan based polarization sensitive SDOCT for retinal imaging," Opt. Lett. 34, 3 (2009).

15. M. Zhao, Y. Huang, and J. U. Kang, "Sapphire ball lens-based fiber probe for common-path optical coherence tomography and its applications in corneal and retinal imaging," Opt. Lett. 37, 3 (2012).

16. S. H. Yun, G. J. Tearney, J. F. d. Boer, N. Iftimia, and B. E. Bouma, "High-speed optical frequency-domain imaging," Opt. Express 11, 11 (2003).

17. L. An and R. K. Wang, "In vivo volumetric imaging of vascular perfusion within human retina and choroids with optical micro-angiography," Opt. Express 16, 15 (2008).

18. W. A. Benalcazar, W. Jung, and S. A. Boppart, "Aberration characterization for the optimal design of high-resolution endoscopic optical coherence tomography catheters," Opt. Lett. 37, 3 (2012).

19. Y. Zhu, N. G. Terry, J. T. Woosley, N. J. Shaheen, and A. Wax, "Design and validation of an angle-resolved low-coherence interferometry fiber probe for in vivo clinical measurements of depth-resolved nuclear morphology," J. Biomed. Opt. 16(2011).

20. Y. Mao, S. Chang, S. Sherif, and C. Flueraru, "Graded-index fiber lens proposed for ultrasmall probes used in biomedical imaging," Appl. Opt 46, 8 (2008).

21. J. U. Kang, J.-H. Han, X. Liu, K. Zhang, C. G. Song, and P. Gehlbach, "Endoscopic Functional Fourier Domain Common-Path Optical Coherence Tomography for Microsurgery," IEEE J. Sel. Top. Quant. Electron. 16, 12 (2010).

22. G. J. Tearney, M. E. Brezinski, B. E. Bouma, S. A. Boppart, C. Pitris, J. F.Southern, and J. G.Fujimoto, "In vivo endoscopic optical biopsy with optical coherence tomography," Science 276, 3 (1997).

23. S. Liang, A. Saidi, J. Jing, G. Liu, J. Li, J. Zhang, C. Sun, J. Narula, and Z. Chen, "Intravascular atherosclerotic imaging with combined fluorescence and optical coherence tomography probe based on a double-clad fiber combiner," J. Biomed. Opt. 17, 3 (2012).

24. X. Li, T. H. Ko, and J. G. Fujimoto, "Intraluminal fiber-optic Doppler imaging catheter for structural and functional optical coherence tomography," Opt. Lett. 26, 3 (2001).

25. V. X. D. Yang, Y. X. Mao, N. Munce, B. Standish, W. Kucharczyk, N. E. Marcon, B. C. Wilson, and I. A. Vitkin, "Interstitial Doppler optical coherence tomography," Opt. Lett. 30, 3 (2005).

26. K. Zhang and J. U. Kang, "Common-path low-coherence interferometry fiber-optic sensor guided microincision " J. Biomed. Opt. 16, 5 (2011).

27. R. Pepperkok, C. Schneider, L. Philipson, and W. Ansorge, "Single cell assay with an automated capillary injection system," Exp. Cell. Res. 17, 8 (1988).

28. S. Mitragotri, "Current status and future prospects of needle-free liquid jet injectors," Nature Rev. Drug Discov. 5, 6 (2006).

29. T. Peters and K. Cleary, *Image-Guided Interventions: Technology and Applications*, Springer, 2008.

30. Zhang, K., Wang, W., Han, J-H., Kang, J. U., "A surface topology and motion compensation system for microsurgery guidance and intervention based on common-path optical coherence tomography," IEEE Trans. Biomed. Eng., 56(9), 2318-2321 (2009).

31. Zhang, K., Akpek, E. K., Weiblinger, R. P., Kim, D-H., Kang, J. U., and Ilev, I. K., "Noninvaseive volumetric quality evaluation of post-surgical clear corneal incision via high-resolution Fourier-domain optical coherence tomography," Electron. Lett., 46(22), 1482-1483 (2010).

32. Zhang, K. and Kang, J. U., "Real-time 4D signal processing and visualization using graphics processing unit on a regular nonlinear-k Fourier-domain OCT system." Opt. Express, 18(11), 11772-11784 (2010).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore understood that, within the scope of the claims and their equivalents, the invention may be practiced otherwise than as specifically described.

We claim:

1. A motion-compensated cutting system comprising:
a tool body having a size and configuration to be used for hand-held operation;
an actuator connected to the tool body, said actuator comprising a shaft that is movable relative to the tool body;
a cutting implement attached to the shaft such that a distal end of the cutting implement is movable relative to the tool body in an axial direction;
a position sensor attached to the tool body and arranged to detect a position of the shaft relative to the tool body;
an optical coherence tomography system comprising a light source and an optical fiber having a distal end fixed relative to the distal end of the cutting implement, wherein the light source of the optical coherence tomography system is configured to generate light for feeding to the position sensor via the optical fiber and a reference surface via another optical fiber;
a coupler configured to combine an optical signal received from the reference surface and an optical signal received from the position sensor;
a detector configured to receive a combination of the optical signal received from the reference surface and the optical signal received from the position sensor and generate an electrical signal based on the combination of the optical signal received from the reference surface and the optical signal received from the position sensor; and
a control unit arranged to be in operative communication with the optical coherence tomography system, the position sensor, and the actuator,
wherein the control unit is configured to determine a position of the distal end of the cutting implement relative to the reference surface based on the electrical signal characterizing the combination of the optical signal received from the reference surface and the optical signal received from the position sensor, and wherein the control unit is further configured to control the actuator to move the cutting implement to compensate for relative motion between the tool body and the reference surface at least during a cutting operation, and wherein the control unit is further configured to maintain a predetermined depth of the distal end of the cutting implement with respect to the reference surface during the cutting operation.

2. The motion-compensated cutting system according to claim 1, wherein the relative motion is caused by a hand tremor of an operator of the cutting system.

3. The motion-compensated cutting system according to claim 1, wherein the control unit is configured to control the actuator during the cutting operation such that the predetermined depth of the distal end of the cutting implement with respect to the reference surface is constant across a length of a cut made by the cutting operation.

4. The motion-compensated cutting system of claim 1:
wherein the control unit is configured to detect deformation of the subject based on a signal from the optical coherence tomography system, the deformation resulting from at least one of movement of the subject, insertion of the cutting implement into the subject, and a movement of the cutting implement along a length of a cut as a cutting operation is performed, and wherein the control unit is configured to control the actuator to compensate for the deformation.

5. The motion-compensated cutting system of claim 1, wherein the position sensor comprises an optical coherence tomography-based encoder.

6. The motion-compensated cutting system of claim 1, wherein the control unit is adapted to be in communication with the position sensor and is configured to, at least one of:
move the shaft, using input from the position sensor, to a reset position after a single cut is completed, or
communicate a warning signal when the shaft is at or near a limit of a range of motion of the shaft.

7. The motion-compensated cutting system of claim 1, wherein the optical coherence tomography system is a common-path optical coherence tomography system.

8. The motion-compensated cutting system of claim 1, wherein the cutting implement and the optical fiber are detachable from a remainder of the motion-compensated cutting system.

9. The motion-compensated cutting system of claim 1, further comprising:
a measuring unit configured to measure a length of a cut performed by the cutting system, wherein a depth of the cut either varies with the length of the cut or remains constant with the length of the cut.

10. The motion-compensated cutting system of claim 9, wherein the measuring unit measures the length of the cut using speckle de-correlation and a duration of the cutting operation.

11. The motion-compensated cutting system according to claim 1, wherein the control unit is configured to control the actuator during the cutting operation such that the predetermined depth of the distal end of the cutting implement with respect to the reference surface varies in a predetermined manner across the length of the cut.

12. A motion-compensated micro-manipulation system, comprising:
a tool body having a size and configuration to be used for manual manipulation;

an actuator connected to the tool body, said actuator comprising a shaft that is movable relative to the tool body;

a tool element attached to the shaft such that a distal end of the tool element is movable relative to the tool body in an axial direction;

a position sensor attached to the tool body and arranged to detect a position of the shaft relative to the tool body;

an optical coherence tomography system comprising a light source and an optical fiber having a distal end fixed relative to the distal end of the tool element, wherein the light source of the optical coherence tomography system is configured to generate light for feeding to the position sensor via the optical fiber and a reference surface via another optical fiber;

a coupler configured to combine an optical signal received from the reference surface and an optical signal received from the position sensor;

a detector configured to receive a combination of the optical signal received from the reference surface and the optical signal received from the position sensor and generate an electrical signal based on the combination of the optical signal received from the reference surface and the optical signal received from the position sensor; and a control unit arranged to be in operative communication with the optical coherence tomography system, the position sensor, and the actuator, wherein the control unit is adapted to be in communication with the position sensor and is configured to, at least one of:
move the shaft, at a predetermined stage of a micro-manipulation procedure, to a reset position using input from the position sensor, or
communicate a warning signal when the shaft is in a predetermined position, and wherein the control unit is further configured to determine a position of the distal end of the tool element relative to the reference surface based on the electrical signal characterizing the combination of the optical signal received from the reference surface and the optical signal received from the position sensor.

13. The motion-compensated micro-manipulation system of claim 12, wherein the control unit controls the actuator to achieve a predetermined distance between the distal end of the tool element and the reference surface.

14. The motion-compensated micro-manipulation system of claim 12, wherein the position sensor comprises an optical coherence tomography-based encoder.

15. The motion-compensated micro-manipulation system of claim 12, wherein the predetermined position of the shaft is at or near a limit of a range of motion of the shaft.

16. The motion-compensated micro-manipulation system of claim 12, further comprising a warning device arranged to receive the warning signal from the control unit, the warning device being configured to communicate a visual or auditory warning to an operator of the micro-manipulation system.

17. The motion-compensated micro-manipulation system of claim 12, wherein the reset position is substantially in a center of a range of motion of the shaft.

18. The motion-compensated micro-manipulation system of claim 12, wherein the predetermined stage is based on exceeding a predetermined distance between the distal end of the tool element and the reference surface.

19. The motion-compensated micro-manipulation system of claim 12, further comprising a control in communication with the control unit,
wherein the control is arranged to be manually operable by an operator of the micromanipulation system, and
wherein the predetermined stage is based on the operator operating the control.

20. The motion-compensated micro-manipulation system of claim 12, wherein the optical coherence tomography system further includes an optical sensor in communication with the optical fiber and configured to receive a signal from the optical fiber.

21. A method of performing a motion-compensated cutting operation, comprising:
providing a cutting tool comprising a tool body and a cutting implement coupled to the tool body, the cutting implement having a distal end configured to cut tissue of a patient;
providing an optical coherence tomography system at least a portion of which is coupled to the cutting tool, the optical coherence tomography system including a light source and an optical fiber having a distal end fixed relative to the distal end of the cutting implement, wherein the light source of the optical coherence tomography system is configured to generate light for feeding to the position sensor via the optical fiber and a reference surface via another optical fiber;
performing the cutting operation by the cutting tool;
controlling a position of the cutting implement along a longitudinal axis of the cutting implement over a duration of the cutting operation based on an input from the optical coherence tomography system to perform a cut of a desired depth;
detecting, by a position sensor, an extent to which the cutting implement is extended relative to the tool body;
combining, by a coupler, an optical signal received from the reference surface and an optical signal received from the position sensor, wherein the optical signal received from the position sensor indicates the extent to which the cutting implement is extended relative to the tool body;
receiving, by a detector, a combination of the optical signal received from the reference surface and the optical signal received from the position sensor and generating an electrical signal based on the combination of the optical signal received from the reference surface and the optical signal received from the position sensor; and
controlling the position of the cutting implement when the extent to which the cutting implement is extended reaches a predetermined value, wherein the controlling is based on the electrical signal characterizing the combination of the optical signal received from the reference surface and the optical signal received from the position sensor.

22. The method of performing the motion-compensated cutting operation according to claim 21, wherein controlling the position of the cutting implement over a duration of the cutting operation includes moving the cutting implement in a repetitive back-and-forth motion along the longitudinal axis of the cutting implement.

* * * * *